United States Patent [19]
Wardlaw

[11] Patent Number: 6,022,734
[45] Date of Patent: Feb. 8, 2000

[54] DISPOSABLE APPARATUS FOR DETERMINING ANTIBIOTIC SENSITIVITY OF BACTERIA

[75] Inventor: Stephen C. Wardlaw, Old Saybrook, Conn.

[73] Assignees: Wardlaw Partners, L.P., Lyme, Conn.; Robert A. Levine, Guilford, Conn.

[21] Appl. No.: 09/256,451

[22] Filed: Feb. 23, 1999

Related U.S. Application Data

[60] Provisional application No. 60/077,216, Mar. 7, 1998.

[51] Int. Cl.$^7$ .................................................. C12M 1/16
[52] U.S. Cl. .................................. 435/288.7; 435/287.7; 435/288.3; 435/288.4
[58] Field of Search ................................. 435/30, 32, 33, 435/287.1, 287.7, 287.8, 287.9, 288.3, 288.4, 288.7, 808, 810; 422/56, 61, 82.05, 82.08

[56] References Cited

U.S. PATENT DOCUMENTS

| | | |
|---|---|---|
| 3,728,228 | 4/1973 | Duranty . |
| 3,826,717 | 7/1974 | Gilbert et al. . |
| 3,925,166 | 12/1975 | Blume . |
| 4,054,490 | 10/1977 | Vesterberg ........................ 195/103.5 K |
| 4,204,045 | 5/1980 | Kjellander et al. . |
| 4,514,495 | 4/1985 | Schalkowsky et al. ................... 435/32 |
| 4,778,758 | 10/1988 | Ericsson et al. . |
| 4,790,640 | 12/1988 | Nason ..................................... 350/534 |
| 4,950,455 | 8/1990 | Smith ....................................... 422/56 |
| 5,028,529 | 7/1991 | Ericcson et al. . |
| 5,164,301 | 11/1992 | Thompson et al. ....................... 435/29 |
| 5,206,151 | 4/1993 | Robertson ................................ 435/32 |
| 5,246,837 | 9/1993 | Schalkowsky ........................... 435/29 |
| 5,427,959 | 6/1995 | Nishimura et al. ..................... 436/534 |
| 5,501,959 | 3/1996 | Lancaster et al. ........................ 435/32 |
| 5,547,849 | 8/1996 | Baer et al. ............................. 435/7.24 |
| 5,563,043 | 10/1996 | Schalkowsky ........................... 435/32 |
| 5,639,632 | 6/1997 | Ericsson et al. . |
| 5,702,684 | 12/1997 | McCoy et al. . |

*Primary Examiner*—William H. Beisner
*Attorney, Agent, or Firm*—William W. Jones

[57] ABSTRACT

A disposable cassette for testing the minimum inhibitory concentration of antibiotic for a target microorganism is provided. The cassette includes a body, a sheet of microorganism growth medium, and a sensible reagent. The sensible reagent, which is incorporated into the sheet of growth medium, includes an antibiotic and a marker, and the marker has a signal with a magnitude proportional to its concentration.

36 Claims, 2 Drawing Sheets

DISPOSABLE APPARATUS FOR DETERMINING ANTIBIOTIC SENSITIVITY OF BACTERIA

This application claims the benefit of U.S. Provisional Application No. 60/077,216, filed Mar. 7, 1998.

BACKGROUND OF THE INVENTION

1. Technical Field

The present invention relates to apparatus for determining a microorganism's sensitivity to an antibiotic in general, and to apparatus for determining the minimum inhibitory concentration of an antibiotic relative to a microorganism in particular.

2. Background Information

The determination of the minimum inhibitory concentration (MIC) of an antibiotic is an essential laboratory test to determine the sensitivity of a microorganism, usually a bacterium, to specific antibiotics. The MIC refers to the minimum concentration of an antibiotic necessary to prevent the microorganism from growing. The type and dose of antibiotics is often predicated upon this type of test, making rapid and accurate results critical to both patient care and cost-effective treatment. Antibiotic sensitivity testing is most commonly performed using the qualitative Kirby-Bauer plate method, but for a quantitative MIC analysis, the tube dilution method is most commonly used.

The Kirby-Bauer test utilizes a plate covered with a uniform layer of microbiological growth medium specifically formulated for the test at hand. A number of disks are placed on the layer of growth medium, each containing a specific concentration of an antibiotic being evaluated. Bacteria grows on the medium forming a visible coating, except in the area (generally referred to as the "clear zone") around those disks having sufficient antibiotic concentration to inhibit bacterial growth. The size of the clear zone surrounding a disk is indicative of the organism's sensitivity to the antibiotic contained in that particular disk; i.e., the larger the clear zone, the greater the organism's sensitivity to the antibiotic contained in the disk. The Kirby-Bauer test is popular because of its simplicity and its ability to evaluate multiple antibiotics at once. A disadvantage of the Kirby-Bauer test is that there are a number of variables which affect the antibiotic concentration at any given point in the growth medium, and thus do not allow a MIC to be calculated. Formulae have been published for calculating the approximate MIC based upon the clear zone size, but these formulae are rarely used and are considered to be approximations at best.

The tube dilution method involves placing an equal amount of target microorganism in a plurality of wells (referred to as "tubes") disposed in a platter, and adding different concentrations of an antibiotic to each tube. The lowest concentration of antibiotic in which the target microorganism will not grow determines the MIC for that particular microorganism. A disadvantage of the tube dilution method is that its accuracy depends on the step size in concentration change between tubes. A small step size yields greater accuracy, but may require an impractical number of tubes and effort. In addition, preparing accurate dilutions is an expensive process that increases in cost with the number of tubes. Hence, increasing the accuracy of this method can also increase the cost and time required.

An alternative means of performing a MIC determination is described in U.S. Pat. No. 4,778,758 and others, which involves the use of an "E-Strip™", which is a strip that incorporates a precisely formed gradient of a single antibiotic typically. Calibration marks are disposed along a side of the strip, corresponding to the exact concentration of the antibiotic at that point. The strip is placed onto an inoculated Kirby-Bauer plate and after incubation a clear area will form contiguous with an area of microorganism growth, provided an antibiotic concentration within the gradient exceeds the MIC. The calibration markings corresponding to the border between the clear area and the growth area give the MIC value for the antibiotic being evaluated. Several disadvantages are associated with this method for determining a MIC of an antibiotic including, but not limited to: 1) the strip is difficult and consequently expensive to manufacture; 2) the size of the strip makes it impractical for concurrent multiple antibiotic tests in a single apparatus; and 3) the preparation must be read after a precise period of incubation to achieve optimum accuracy.

U.S. Pat. No. 5,702,684 discloses a method for monitoring antibiotic levels for determining when the antibiotics should be replenished in an industrial plumbing system using a fluorescent marker. This method, however, does not allow the determination of a MIC or any type of antibiotic sensitivity measurement.

What is needed is an apparatus for determining the MIC of an antibiotic for a target microorganism, one that can determine the MIC in a minimum amount of time, one that provides an accurate MIC, one that can simultaneously determine the MIC's of several antibiotics for a target microorganism, and one that is cost effective.

DISCLOSURE OF THE INVENTION

It is, therefore, an object of the present invention to provide an apparatus for determining the MIC of an antibiotic for a target microoranism that provides an accurate result in a minimum amount of time.

It is another object of the present invention to provide an apparatus for determining the MIC's of several antibiotics for a target microorganism.

It is another object of the present invention to provide a cost effective apparatus for determining the MIC of an antibiotic for a target microorganism.

It is another object of the present invention to provide an apparatus for determining the MIC of an antibiotic for a target microorganism that has utility in veterinary medicine.

According to the present invention, an apparatus for testing the minimum inhibitory concentration of antibiotic for a target microorganism includes a body, a sheet of microorganism growth medium, and a sensible reagent. The body includes a well for receiving the sheet of microorganism growth medium. The sensible reagent, which is incorporated into the sheet of growth medium, includes an antibiotic and a marker, and the marker has a sensible signal proportional to its concentration. The terms "proportion" and "proportional" as used within the present specification comprise any relationship that can be mathematically described; e.g., $x$:$y$, $x$:$y^2$, $x$:$^1/y$, etc.

An advantage of the present invention is that an apparatus for determining the MIC of an antibiotic for a target microorganism is provided that gives accurate results in a minimum amount of time. The present invention uses a sensible reagent including a marker having a signal proportional to its concentration which, in turn, is proportional to the concentration of the antibiotic. The MIC of antibiotic at the growth boundary can be determined by sensing the marker signal at the growth boundary. Accordingly, the exact MIC of antibiotic can be determined rather than an approximation, and can be determined without a multitude of time consuming dilution steps.

Another advantage of the present invention is that the MIC's of several antibiotics for a target microorganism can be determined concurrently using the present invention. For example, a number of independent growth medium regions inoculated with a target microorganism (i.e., the "active areas" of the growth medium) can be plated in a single cassette, and a different antibiotic applied to each independent region. Each active area can then be evaluated to ascertain the MIC of the particular antibiotic in that active area.

Another advantage of the present invention is that a cost effective apparatus for determining the MIC of an antibiotic for a target microorganism is provided. The ability of the present invention method to provide accurate MIC information obviates the need for multiple expensive antibiotic dilutions as are required in the tube dilution method. A person of skill in the art will recognize that minimizing expensive medical laboratory time and laboratory assets make the present invention method considerably less expensive than presently available methods.

Another advantage of the present invention is that a "user-friendly" apparatus for determining the MIC of an antibiotic for a target microorganism is provided. The present invention cassette facilitates the MIC testing, particularly multiple MIC tests, minimizes the opportunity for sample spillage, and can be readily disposed of after the test. These qualities and others make the present invention cassette attractive as a disposable.

These and other objects, features and advantages of the present invention will become apparent in light of the detailed description of the best mode embodiment thereof, as illustrated in the accompanying drawings.

BEST MODE FOR CARRYING OUT THE INVENTION

Figure 1:
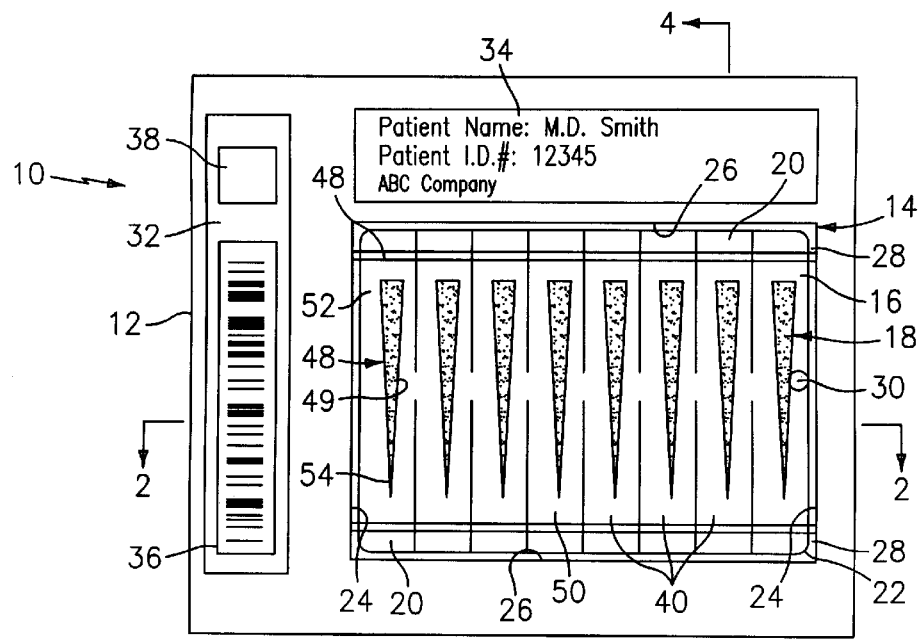
FIG. 1 is a diagrammatic view of the present invention cassette.
Figure 2:
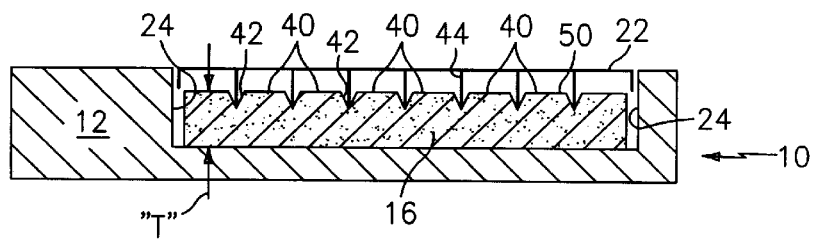
FIG. 2 is a width-wise cross-sectional view of the cassette shown in FIG. 1.
Figure 3:
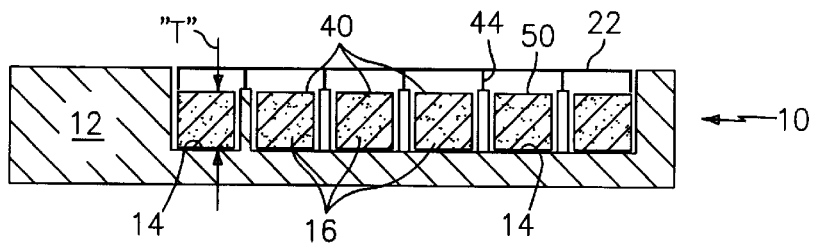
FIG. 3 is a cross-sectional view similar to that shown in FIG. 2, illustrating a cassette embodiment having a plurality of wells.
Figure 4:
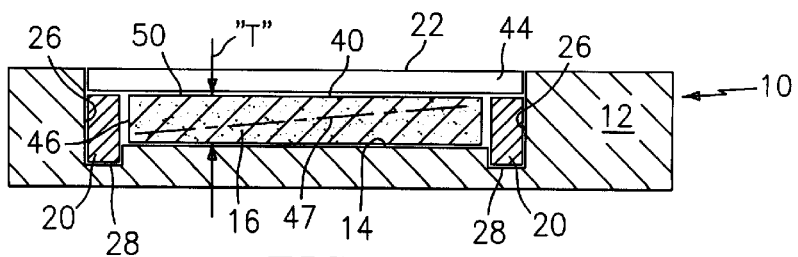
FIG. 4 is a length-wise cross sectional view of the cassette shown in FIG. 1.
Figure 5:
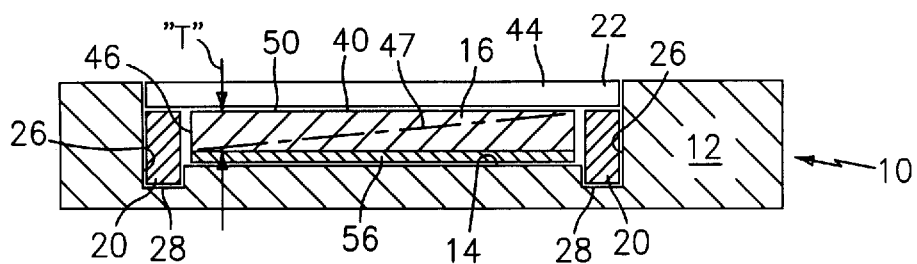
FIG. 5 is a length-wise cross sectional view of the cassette, including sensible reagent applied to a substrate in contact with the growth medium.

Referring to FIG. 1, an apparatus 10 for use in testing the minimum inhibitory concentration of antibiotic for a target microorganism sample (hereinafter referred to as a "cassette") includes a body 12 having a well 14, a sheet of microorganism growth medium 16, a sensible reagent 18 incorporated into the growth medium 16, a pair of absorbent strips 20, and a transparent well cap 22. The well 14 includes a pair of side walls 24, a pair of end walls 26, and a pair of channels 28 extending between the side walls 24, one channel 28 adjacent each end wall 26. The growth medium 16 is disposed in the well 14, extending between the two channels 28, and one absorbent strip 20 is placed in each channel 28. The transparent well cap 22 attaches to the body 12 above the well 14 to protect and maintain the growth medium 16 and absorbent strips 20 inside the well 14. In an alternative embodiment (see FIG. 3), the body 12 includes a plurality of wells 14, each similar to that described above. A port 30 (FIG. 1) through which a target microorganism solution can be distributed to the growth medium 16 is disposed in the well cap 22. The port 30 may alternatively be disposed in the body 12 of the cassette 10, or be formed between the body 12 and the well cap 22.

The cassette 10 further includes a machine readable information label 32 and a user readable information label 34. The machine readable information label 32 includes a data block 36 containing pertinent information such as the test to be performed, calibration constants, patient identification, or the like, in a machine readable format such as a bar code or magnetic strip. Depending upon the analysis application, the machine readable label 32 may directly contain all of the information necessary to enable an analytical device 61 to perform the analysis at hand. In other instances, the machine readable label 32 may instruct the analytical device 61 to access data files contained within the analytical device or remotely accessed by the analytical device. Hence, it can be said that the label 32 directly or indirectly contains the information necessary to enable an analytical device 61 to perform the analysis at hand. The function of the analytical device 61 is described in more detail below. The machine readable information label 32 may also include a reference pad 38 containing a known amount of a sensible marker for use in analyzing the reagent marker signal (discussed in detail below) within the growth medium 16. The sensible marker contained within the reference pad 38 may be different from that used within the reagent 18. The user readable information label 34 includes information that enables the cassette 10 to be identified by the user without machine assistance.

The sheet of growth medium 16 is preferably a hydroscopic material such as polyvinyl alcohol, hydroxyethyl starch, phytagel, modified agar, or the like, which is admixed with materials capable of sustaining growth of the target microorganism and may also contain agents which serve to highlight microbial growth. Examples of such agents include general growth indicators such as disclosed in U.S. Pat. Nos. 4,049,099 and 5,501,959. Dehydrated growth mediums 16 that may be rehydrated during use are favored because they can be readily stored for extended periods of time. The sheet of growth medium 16 has a uniform thickness "T" (see FIGS. 2–5) in the areas 40, referred to as the "active" areas 40, where the sensible reagent 18 is incorporated. In one embodiment, the active areas 40 of the growth medium sheet 16 are separated by trenches 42, thereby forming rows of active areas 40. Dividers 44 can be attached to the well cap 22 to help separate adjacent active areas 40.

The sensible reagent 18 includes the antibiotic to be evaluated and a marker. In a first embodiment, the sensible reagent 18 contains an exact quantity of the antibiotic to be evaluated mixed with a useful, but imprecisely measured, quantity of marker. In a second embodiment, the antibiotic and the marker of the sensible reagent 18 are mixed in a known ratio, and the overall quantity of the reagent is varied to suit the application. Both sensible reagent 18 embodiments require only one parameter (antibiotic quantity or antibiotic to marker ratio) to be known accurately, thus minimizing the cost of manufacturing the sensible reagent 18 and consequently the cassette 10. The marker may be any material that: 1) has an identifiable signal proportional to its concentration; 2) has a signal that is distinguishable from other elements within the test sample; 3) has a signal that is not adversely affected by growth of the target microorganism; 4) does not substantially adversely effect growth of the target microorganism; 5) does not unpredictably or adversely affect the action of the antibiotic being evaluated; and 6) one which will co-diffuse with the antibiotic in the growth medium 16 during the incubation period in a predictable manner so that the local marker concentration is proportional to the local antibiotic concentration. For example, a fluorescent marker having excitation or emission wavelengths outside the range of the excitation or emission wavelengths of the growth medium, and one that does not bind to the growth medium 16 or the target microorganism may be used.

The sensible reagent 18 may be directly or indirectly incorporated into the growth medium 16. Direct incorporation may be accomplished by several methods including, but not limited to, injecting the sensible reagent 18 into the growth medium 16, or applying the reagent 18 onto a surface of the growth medium 16 and allowing the reagent 18 to diffuse into the growth medium 16. Injecting the sensible reagent 18 into the growth medium 16 may be advantageous for a reagent 18 with a low diffusion rate (once in the growth medium 16, the reagent 18 can diffuse locally to form a desirable concentration gradient). Applying the sensible reagent 18 onto a surface of the growth medium 16, on the other hand, may be adequate for readily diffusing reagents. For example, a reagent 18 having a high diffusion rate relative to a particular growth medium 16 may be placed in contact with an end surface 46 (see FIGS. 1 and 4) of the growth medium 18, where it will diffuse laterally into the growth medium 16. The diffusion creates a desirable gradient 47 of reagent concentration within the growth medium 16 (shown diagrammatically in FIGS. 4 and 5 as a phantom line). To ensure the formation of the desirable gradient 47, however, it is preferable to apply the sensible 18 reagent as a strip 48 onto a face surface 50 of the growth medium 16. At a first end 52, the strip 48 has a first quantity of sensible reagent 18 which, when incorporated into the growth medium 16, will create an antibiotic concentration sufficient to inhibit growth of the target microorganism within the growth medium 16. At a second end 54, the strip 48 has a second quantity of sensible reagent which, when incorporated into the growth medium 16, will create an antibiotic concentration insufficient to inhibit growth of the target microorganism within the growth medium 16. The first quantity of reagent 18 is greater than the second quantity, and a gradient 49 of decreasing reagent quantities extends between the first and second ends 52,54. Indirect incorporation may be accomplished by applying the sensible reagent 18 onto a substrate 56 (see FIG. 5; preferably in the form of a strip 48 as described above) and subsequently placing the substrate 56 in contact with the growth medium 16.

A reagent strip 48 on the surface of the growth medium 16 (or substrate 56) may be formed by a variety of processes. For example, a plurality of droplets of the sensible reagent deposited on the growth medium 16 (or on a substrate 56 to be placed into contact with the growth medium 16) can be smeared in parallel lines of reagent 18, decreasing in quantity to form the desirable quantity gradient 49. Alternatively, the reagent strips 48 can be formed by a spray-type or printing-type process such as inkjet printing. Sensible reagent 18 injected into the growth medium 16 may be injected in a "strip" manner as described above to facilitate the formation of a reagent quantity gradient 49 (and therefore a reagent concentration gradient 47) within the growth medium 16.

The marker and the antibiotic of the sensible reagent 18 preferably diffuse within the growth medium 16 at the same rate, although a similar diffusion rate is not required. A marker and an antibiotic having different but known diffusion rates may be used alternatively. In another example, an identifiable dye that is absorbed by the antibiotic may be used. In this case, the marker signal emitted from the dye is proportional to the concentration of antibiotic since it is the antibiotic that is "carrying" the dye.

Figure 6:
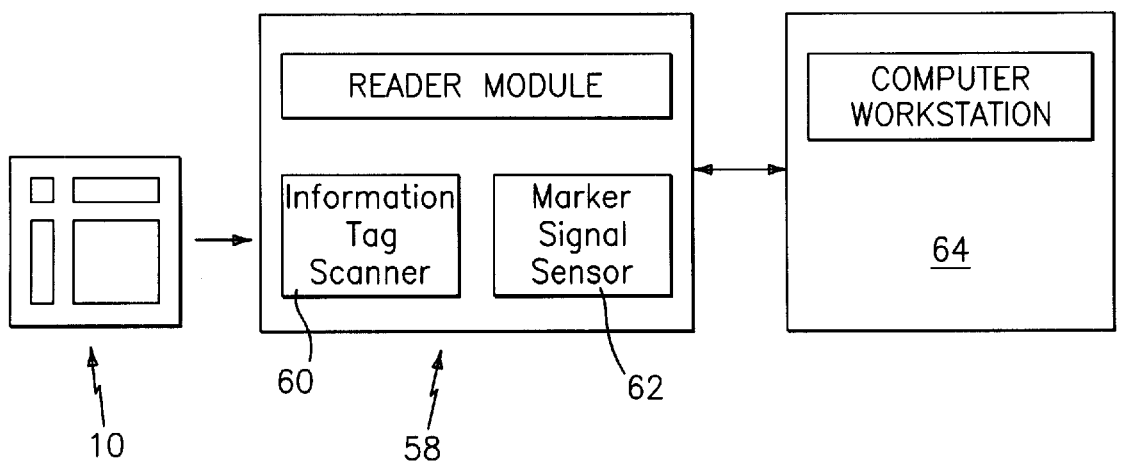
FIG. 6 is a diagram of the system for determining the minimum inhibitory concentration of an antibiotic for a target microorganism.

Referred to FIGS. 1 and 6, the above described cassette 10 is designed to facilitate the determination of the minimum inhibitory concentration (MIC) for antibiotics for a target microorganism. To perform the MIC test, the user adds a liquid solution (not shown) containing the target microorganism to the growth medium 16 via the port 30. The target microorganism may consist of either first generation microbes taken, for example, from a urine sample, or a suspension of microbes taken, for example, from a colony grown on another growth medium. The solution permeates the growth medium 16 and thereby inoculates it with the target microorganism. Excess solution is absorbed by the absorbent strips 20 disposed in the channels 28 adjacent the end walls 26 of the well 14. Absorbing the excess solution minimizes the opportunity for undesirable solution spill outside of the cassette 10. In the case of a dehydrated growth medium 16, the solution hydrates the growth medium 16 and causes the sensible reagent 18 to diffuse within the growth medium 16 thereby creating a gradient 47 of reagent concentrations within the growth medium 16.

The growth medium 16, incorporating the sensible reagent 18, inoculated with the target microorganism, and housed within the cassette 10, can be incubated under any conditions that are acceptable to the growth medium 16 and the target microorganism. These conditions generally include incubation at 35 degrees Centigrade and in an atmosphere having an elevated carbon dioxide content. The growth medium 16 is typically incubated at 35 degrees Centigrade until a section of growth medium 16 has detectable target microorganism growth. The section of growth medium 16 having detectable target microorganism growth will be contiguous with a section of growth medium 16 having substantially no detectable target microorganism growth. The border between the two sections is referred to as the growth boundary. The section of growth medium 16 having detectable growth of target microorganism is that in which the target microorganism is substantially uninhibited by the antibiotic. In contrast, the section having no detectable growth is that in which the microorganism is substantially inhibited by the antibiotic. The growth boundary coincides with the MIC of the antibiotic for the target microorganism being evaluated.

Referring to FIGS. 1 and 6, the cassette 10 is usable with an analytical device 61 having a reader module 58 and a computer workstation 64. The reader module 58, which accepts the cassette 10, includes a scanner 60 for reading the machine readable information label 32 and a sensor 62 capable of detecting the marker signal at the growth boundary. The reader module 58 is preferably connected to a computer workstation 64 having a central processing unit (CPU) programmed for the task at hand. Separability between the reader module 58 and the computer workstation 64 enables the reader module 58 to be considered an input device to the computer workstation 64, thereby facilitating upgrades of either device should any become desirable. The machine readable information label 32 is scanned and pertinent data is transferred to the computer workstation 64.

In all embodiments, the computer workstation 58 directs the sensor 62 to scan the cassette 10 to determine marker signal magnitude over the entire growth medium 16 active area(s) 40. An algorithm programmed within the computer workstation 64 accepts the data from the reader module 58 and uses that data to calculate the antibiotic concentration at the growth boundary, which corresponds to the minimum inhibitory concentration (MIC) of the antibiotic for the particular target microorganism at hand. A more detailed explanation of the calculations can be found in applicant's co-pending U.S. patent application Ser. No. 09/255,681.

Although this invention has been shown and described with respect to the detailed embodiments thereof, it will be understood by those skilled in the art that various changes in form and detail thereof may be made without departing from the spirit and the scope of the invention.

I claim:

1. An apparatus for testing the minimum inhibitory concentration of antibiotic for a target microorganism sample, said apparatus comprising:

a body;

a sheet of microorganism growth medium attached to said body; and a sensible reagent, incorporated into said sheet of growth medium, having an antibiotic and a marker, said marker having a signal with a magnitude proportional to its concentration;

wherein the concentration of said antibiotic is determinable from said signal.

2. An apparatus according to claim 1, wherein said body further comprises a well, wherein said sheet of growth medium is disposed in said well.

3. An apparatus according to claim 2, wherein said sensible reagent is applied to a surface of said growth medium and incorporated into said growth medium from said surface.

4. An apparatus according to claim 3, wherein said sensible reagent is applied in a strip, said strip having a first quantity of reagent at a first end, a second quantity of reagent at a second end, said first quantity greater than said second quantity, and a gradient of decreasing reagent quantities between said first and second ends.

5. An apparatus according to claim 2, wherein said sensible reagent is applied to a substrate and said substrate is placed in contact with, or in close proximity to, said growth medium, wherein said reagent incorporates into said growth medium from said substrate.

6. An apparatus according to claim 5, wherein said sensible reagent is applied in a strip, said strip having a first quantity of reagent at a first end, a second quantity of reagent at a second end, said first quantity greater than said second quantity, and a gradient of decreasing reagent quantities between said first and second ends.

7. An apparatus according to claim 2, further comprising: a machine readable information label, said label directly or indirectly containing information relating to said minimum inhibitory concentration testing.

8. An apparatus according to claim 7, wherein said machine readable label further comprises a reference pad containing a known amount of a sensible reference marker.

9. An apparatus according to claim 2, further comprising: a user readable information label, said label containing information relating to said minimum inhibitory concentration testing.

10. An apparatus for testing the minimum inhibitory concentration of antibiotic for a target microorganism sample, said apparatus comprising:

a body, having a well;

a sheet of microorganism growth medium, disposed in said well, said sheet having a plurality of active areas; and a plurality of sensible reagents, each incorporated into one of said active areas, and each reagent having an antibiotic and a marker, each said marker having a signal with a magnitude proportional to its concentration;

wherein the concentration of each reagent's antibiotic is determinable from said signal of said same reagent's marker.

11. An apparatus according to claim 10, wherein said sensible reagents are applied to a substrate and said substrate is placed in contact with or in close proximity to said growth medium, wherein said reagents incorporate into said growth medium from said substrate.

12. An apparatus according to claim 10 wherein said antibiotic of each said reagent is different from said antibiotic of each other said reagent.

13. An apparatus according to claim 12, wherein each said sensible reagent is applied to a surface of one of said active areas and incorporated into said growth medium through said surface.

14. An apparatus according to claim 13, wherein each said sensible reagent is applied in a strip, each said strip having a first quantity of reagent at a first end, a second quantity of reagent at a second end, said first quantity greater than said second quantity, and a gradient of decreasing reagent quantities between said first and second ends.

15. An apparatus according to claim 14, wherein said growth medium further comprises a trench disposed between adjacent said active areas.

16. An apparatus according to claim 15, further comprising a transparent well cap, said well cap attached to said body over said well.

17. An apparatus according to claim 16, wherein said transparent well cap comprises at least one divider, said divider extending into said trench.

18. An apparatus according to claim 17, wherein said transparent well cap includes a feed slot through which the target microorganism sample is added to said apparatus.

19. An apparatus according to claim 18, wherein said growth medium is dehydrated prior to use.

20. An apparatus according to claim 19, further comprising at least one channel disposed in said well, wherein excess target microorganism sample collects in said channel.

21. An apparatus according to claim 20, further comprising at least one strip of absorbent material, said absorbent material strip disposed in said channel.

22. An apparatus according to claim 10, wherein said growth medium is dehydrated prior to use.

23. An apparatus according to claim 22, further comprising at least one channel disposed in said well, wherein excess target microorganism sample collects in said channel.

24. An apparatus according to claim 23, further comprising at least one strip of absorbent material, said absorbent material strip disposed in said channel.

25. An apparatus for testing the minimum inhibitory concentration of antibiotic for a target microorganism sample, said apparatus comprising:

a body, having a plurality of wells;

a plurality of microorganism growth medium sheets, each sheet disposed in one of said wells;

a plurality of sensible reagents, each incorporated into one of said growth medium sheets, wherein each reagent includes an antibiotic and a marker, each said marker having a signal with a magnitude proportional to its concentration;

wherein the concentration of each reagent's antibiotic is determinable from said signal of said same reagent's marker.

26. An apparatus according to claim 25, wherein each said sensible reagent is applied to a substrate and said substrate is placed in contact with, or in close proximity to, one of said growth medium sheets, wherein said reagents incorporate into said growth medium sheets from said substrates.

27. An apparatus according to claim 25, wherein said antibiotic of each said reagent is different from said antibiotic of each other said reagent.

28. An apparatus according to claim 27, wherein each said sensible reagent is applied to a surface of said growth medium sheet and incorporates into said growth medium through said surface.

29. An apparatus according to claim 28, wherein each said sensible reagent is applied in a strip, each said strip having a first quantity of reagent at a first end, a second quantity of reagent at a second end, said first quantity greater than said second quantity, and a gradient of decreasing reagent quantities between said first and second ends.

30. An apparatus according to claim 29, further comprising a transparent well cap, said well cap attached to said body over said wells.

31. An apparatus according to claim 30, wherein said transparent well cap comprises at least one divider, said divider aligned between adjacent said wells.

32. An apparatus according to claim 31, wherein said growth medium is dehydrated prior to use.

33. An apparatus according to claim 32, further comprising at least one channel disposed in each said well, wherein excess target microorganism sample collects in said channel.

34. An apparatus according to claim 33, further comprising at least one strip of absorbent material, said absorbent material strip disposed in said channel.

35. An apparatus according to claim 25, further comprising:
   a machine readable information label, said label directly or indirectly containing information relating to said minimum inhibitory concentration testing.

36. An antibiotic test container, comprising:
   a body;
   a sheet of microorganism growth medium attached to said body; and
   a sensible reagent incorporated into said sheet of growth medium, said sensible reagent having an antibiotic and a marker, said marker having a signal with a magnitude proportional to its concentration;
   wherein said antibiotic has a concentration proportional to said marker concentration.

* * * * *